(12) United States Patent
Tanaka et al.

(10) Patent No.: US 11,371,172 B2
(45) Date of Patent: Jun. 28, 2022

(54) TUBULAR WOVEN FABRIC

(71) Applicant: Toray Industries, Inc., Tokyo (JP)

(72) Inventors: Nobuaki Tanaka, Otsu (JP); Hiroshi Tsuchikura, Otsu (JP); Satoshi Yamada, Otsu (JP); Yuichi Koyamatsu, Otsu (JP); Taisuke Kogawa, Otsu (JP); Yuka Sakaguchi, Otsu (JP); Kazuhiro Tanahashi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 538 days.

(21) Appl. No.: 16/340,081

(22) PCT Filed: Sep. 29, 2017

(86) PCT No.: PCT/JP2017/035530
§ 371 (c)(1),
(2) Date: Apr. 5, 2019

(87) PCT Pub. No.: WO2018/066476
PCT Pub. Date: Apr. 12, 2018

(65) Prior Publication Data
US 2021/0007838 A1  Jan. 14, 2021

(30) Foreign Application Priority Data

Oct. 7, 2016 (JP) .............................. JP2016-199137
Nov. 30, 2016 (JP) .............................. JP2016-232444

(51) Int. Cl.
*A61F 2/06* (2013.01)
*D03D 3/02* (2006.01)
(Continued)

(52) U.S. Cl.
CPC ................. *D03D 3/02* (2013.01); *A61F 2/06* (2013.01); *A61L 27/20* (2013.01); *A61L 27/222* (2013.01);
(Continued)

(58) Field of Classification Search
CPC ................ A61F 2/06; A61F 2230/0069; A61F 2250/0039; A61F 2/0077;
(Continued)

(56) References Cited

U.S. PATENT DOCUMENTS 4,784,659 A  11/1988 Fleckenstein et al.
4,902,290 A   2/1990 Fleckenstein et al.
(Continued)

FOREIGN PATENT DOCUMENTS

JP  62-55426 B2  11/1987
JP  64-34360 A    2/1989
(Continued)

OTHER PUBLICATIONS

The Extended European Search Report dated Aug. 19, 2020, of counterpart European Application No. 17858314.2.
(Continued)

*Primary Examiner* — Brian E Pellegrino
(74) *Attorney, Agent, or Firm* — DLA Piper LLP (US)

(57) ABSTRACT

A tubular woven fabric is useful as a transport hose for a fluid or a powder, as a protective hose for linear bodies such as wires, cables and conduits, as a tubular filter, or as a base material of a vascular prosthesis. The tubular woven fabric includes warp yarns and weft yarns interwoven with each other, the tubular woven fabric having an outer diameter with a variation of within 10% along the warp direction and satisfying the formula:

$(L2-L1)/L1 \leq 0.1$.

13 Claims, 2 Drawing Sheets

(51) Int. Cl.
  *D03D 15/33* (2021.01)
  *A61L 27/20* (2006.01)
  *A61L 27/22* (2006.01)
  *A61L 27/24* (2006.01)
  *A61L 27/50* (2006.01)
  *A61L 27/58* (2006.01)
  *A61L 33/00* (2006.01)
  *A61L 33/02* (2006.01)
  *D03D 1/00* (2006.01)

(52) U.S. Cl.
  CPC ............. *A61L 27/227* (2013.01); *A61L 27/24* (2013.01); *A61L 27/507* (2013.01); *A61L 27/58* (2013.01); *A61L 33/0041* (2013.01); *A61L 33/027* (2013.01); *D03D 1/0043* (2021.05); *D03D 15/33* (2021.01); *A61F 2210/0004* (2013.01); *A61F 2250/0067* (2013.01); *D10B 2211/06* (2013.01); *D10B 2331/04* (2013.01); *D10B 2509/06* (2013.01)

(58) Field of Classification Search
  CPC ... A61F 2002/30914; A61F 2/07; D03D 3/02; A61L 33/027; A61L 33/0041
  See application file for complete search history.

(56) References Cited

U.S. PATENT DOCUMENTS

| | | | |
|---|---|---|---|
| 5,178,630 | A | 1/1993 | Schmitt |
| 5,282,846 | A | 2/1994 | Schmitt |
| 5,509,931 | A | 4/1996 | Schmitt |
| 5,986,168 | A | 11/1999 | Noishiki |
| 6,117,535 | A * | 9/2000 | Szycher ............... A61F 2/06 428/297.7 |
| 6,461,665 | B1 | 10/2002 | Scholander |
| 2005/0070479 | A1 | 3/2005 | Steinmetzer et al. |
| 2006/0085063 | A1* | 4/2006 | Shastri ............... A61L 27/34 623/1.41 |
| 2010/0100170 | A1* | 4/2010 | Tan ............... A61F 2/07 623/1.18 |
| 2010/0176048 | A1 | 7/2010 | Sakaguchi et al. |
| 2014/0113091 | A1 | 4/2014 | Sakaguchi et al. |
| 2015/0039074 | A1* | 2/2015 | Shalev ............... A61F 2/954 623/1.11 |
| 2015/0224232 | A1 | 8/2015 | Noishiki |
| 2016/0067066 | A1 | 3/2016 | Tanahashi et al. |
| 2016/0206323 | A1* | 7/2016 | Hebert ............ A61B 17/12118 |
| 2017/0157303 | A1* | 6/2017 | Fujita ............... A61L 33/0041 |

FOREIGN PATENT DOCUMENTS

| | | |
|---|---|---|
| JP | 1-51263 B2 | 11/1989 |
| JP | 6-24587 B2 | 4/1994 |
| JP | 7-265338 A | 10/1995 |
| JP | 8-24686 B2 | 3/1996 |
| JP | 8-80342 A | 3/1996 |
| JP | 2960586 B2 | 10/1999 |
| JP | 3497612 B2 | 2/2004 |
| JP | 2005-261867 A | 9/2005 |
| JP | 3799626 B2 | 7/2006 |
| JP | 4152075 B2 | 9/2008 |
| JP | 2009-545333 A | 12/2009 |
| JP | 4461217 B2 | 5/2010 |
| WO | 94/24960 A1 | 11/1994 |
| WO | 2008/032758 | 3/2008 |
| WO | 2012/176861 | 12/2012 |
| WO | 2014/038219 A1 | 3/2014 |
| WO | 2014/168197 A1 | 10/2014 |

OTHER PUBLICATIONS

Mokhtar, S. et al., "Optimization of textile parameters of plain woven vascular prostheses," *The Journal of The Textile Institute*, 2010, vol. 101, No. 12, pp. 1095-1105.

* cited by examiner

TUBULAR WOVEN FABRIC

TECHNICAL FIELD

This disclosure relates to a tubular woven fabric, in particular, a tubular woven fabric useful as a transport hose for a fluid or a powder, as a protective hose for linear bodies such as wires, cables and conduits, as a tubular filter, or as a base material of a vascular prosthesis.

BACKGROUND

Tubular woven fabrics are used for various industrial applications such as hoses, reinforcements and protective materials. Depending on the usage, tubular woven fabrics are bent, wound in a spiral manner, or disposed in a meandering manner to fit the space. To prevent flattening or twisting of tubular woven fabrics in various usages, kink resistance (pliability) is increased by various proposed methods.

JP H06-24587 B, for example, discloses a technique of providing a crimped vascular prosthesis made of a fabric of thermoplastic resin fibers, wherein the vascular prosthesis has a particular corrugated shape and due to this, it has flexibility, allows easy penetration of a suture needle and slightly elongates with time.

JP Patent No. 2960586 discloses a technique of providing a woven vascular prosthesis that does not tend to unravel when cut, does not require crimping and will be self-supporting and maintain an open lumen. The woven vascular prosthesis comprises a plurality of warp yarns woven with a weft yarn to form a weave. The woven fabric contains a fusible component melted to render the woven fabric ravel-resistant. The weft yarn contains a stiffening component that renders the woven fabric self-supporting, and accordingly, the woven fabric does not require crimping over the length.

Vascular prostheses are required to have flexibility to be easily implanted in a curved region in the body and follow the movement of the surrounding tissues after implantation into the body. However, vascular prostheses with flexibility provided by, for example, reducing the fiber density or using microfibers tend to leak blood from the voids between the fibers. Accordingly, various methods of preventing leakage of blood have been proposed. JP Patent No. 1450789, JP H01-34360 A and JP Patent No. 1563185 have reported a method of preventing leakage of blood by filling the voids between the fibers with a bioabsorbable gel such as collagen and gelatin.

The vascular prosthesis of JP H06-24587 B made of a fabric of thermoplastic resin fibers is crimped and consequently has a highly irregular inner surface. Therefore, when the inner diameter of the vascular prosthesis is small, the irregular surface may cause turbulent flow of blood and thrombus formation.

The woven vascular prosthesis of JP Patent No. 2960586 does not require crimping and has a smooth inner surface that is ravel-resistant. The weft yarn containing a fusible component is heat set in the post-processing. The melted weft yarn is fused with the warp yarns and becomes finer, thereby imparting stretch and ravel resistance to the vascular prosthesis. However, according to that technique, the fusible component is not uniformly fused with the warp yarns, and unwanted pores are formed at the intersections between the fine weft yarn and the warp yarns.

JP Patent No. 1450789 proposes that a vascular prosthesis made of a flexible tube with a tensile strength of 20 kg/cm² or more is coated with collagen or gelatin to prevent leakage of blood. However, the tube is too stiff in itself to allow the vascular prosthesis to follow the movement of the surrounding organs. Also, due to the stiffness, the vascular prosthesis cannot be readily sutured into a narrow operative field, and it is also difficult to freely choose where to anastomose the vascular prosthesis.

JP H01-34360 A and JP Patent No. 1563185 disclose that a porous vascular prosthesis can be coated with gelatin to prevent leakage of blood. However, those disclosures fail to define the specific structure of a gelatin coating capable of achieving the required mechanical characteristics and blood leakage prevention.

It could therefore be helpful to provide a tubular woven fabric and a vascular prosthesis that have a less irregular inner surface and exhibit excellent stretch, flexibility and kink resistance (pliability), in particular, a vascular prosthesis that achieves good mechanical characteristics and causes very little blood leakage.

SUMMARY

We thus provide:

(1) A tubular woven fabric comprising warp yarns and weft yarns interwoven with each other, the tubular woven fabric having an outer diameter with a variation of within 10% along the warp direction and satisfying formula (1):

$$(L2-L1)/L1 \geq 0.1 \tag{1}$$

wherein

L1 is a gauge length of the tubular woven fabric when compressed in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric; and L2 is a gauge length of the tubular woven fabric when elongated in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric.

(2) The tubular woven fabric according to the above (1), which has a change index (c) of 0.03 or more and less than 0.2, as determined by formula (2):

$$\text{Change index, } c=(a-b)/a \tag{2}$$

wherein a is a maximum outer diameter of the tubular woven fabric when compressed in the warp direction by applying a stress of 0.01 cN/dtex, and b is a minimum outer diameter of the tubular woven fabric when elongated in the warp direction by applying a stress of 0.01 cN/dtex.

(3) The tubular woven fabric according to the above (1) or (2), which has an inner surface with an irregularity of 100 µm or less.

(4) The tubular woven fabric according to any one of the above (1) to (3), which has no circumferential corrugations.

(5) The tubular woven fabric according to any one of the above (1) to (4), wherein the warp and weft yarns constituting the tubular woven fabric are synthetic fiber yarns.

(6) The tubular woven fabric according to the above (5), wherein the synthetic fiber yarns constituting the tubular woven fabric are non-elastic polyester yarns.

(7) The tubular woven fabric according to the above (5) or (6), wherein the synthetic fiber yarns serving as the warp yarns constituting the tubular woven fabric are multifilament yarns containing filaments, wherein a part or all of the filaments have a diameter of 5 µm or less.

(8) A vascular prosthesis comprising the tubular woven fabric according to any one of the above (1) to (7) as a base material.

(9) A vascular prosthesis comprising the tubular woven fabric according to any one of the above (1) to (7) as a base material, the base material having an inner surface having a layer of an antithrombogenic material.

(10) The vascular prosthesis according to the above (9), wherein the antithrombogenic material contains a sulfur-containing anionic compound having anticoagulant activity.

(11) The vascular prosthesis according to the above (9) or (10), wherein the antithrombogenic material contains a cationic polymer containing, as a monomer unit, a compound selected from the group consisting of alkylene imines, vinyl amines, allylamine, lysine, protamines, and diallyl dimethyl ammonium chloride, and wherein the cationic polymer is covalently bound to warp and weft yarns constituting the tubular woven fabric having an inner surface to be in contact with blood.

(12) A vascular prosthesis comprising the tubular woven fabric according to any one of the above (8) to (11) as a base material, the base material having an outer surface having a layer of a bioabsorbable material.

(13) The vascular prosthesis according to the above (12), which has a kink radius of 15 mm or less.

(14) The vascular prosthesis according to the above (12) or (13), which has a water permeability of 10 mL/cm$^2$·min or less as measured by applying a pressure of 120 mmHg to an inner surface of the vascular prosthesis at 25° C.

(15) The vascular prosthesis according to any one of the above (12) to (14), wherein the bioabsorbable material is a homopolymer or copolymer containing a monomer unit selected from the group consisting of lactic acid, glycolic acid, caproic acid, oxalic acid, malonic acid, succinic acid, glutaric acid, maleic acid, fumaric acid, ethylene glycol, propylene glycol, vinylpyrrolidone and vinyl alcohol.

(16) The vascular prosthesis according to any one of the above (12) to (15), wherein the bioabsorbable material is a polysaccharide or a protein.

(17) The vascular prosthesis according to the above (16), wherein the protein is selected from the group consisting of collagen, atelocollagen and gelatin.

We provide a tubular woven fabric having a less irregular inner surface and exhibiting excellent stretch, flexibility and kink resistance (pliability). The tubular woven fabric is useful as a transport hose for a fluid or a powder, as a protective hose for linear bodies such as wires, cables and conduits, as a tubular filter, or as a base material of a vascular prosthesis. The tubular woven fabric is especially useful for use in a vascular prosthesis. The vascular prosthesis maintains flexibility even when implanted in a curved region, causes no leakage of blood from the voids between the fibers, and is also suitable for emergency surgery.

REFERENCE SIGNS LIST

1 Tubular woven fabric
2 First gauge mark
3 Second gauge mark
4 Load gauge
5 Platform
6 Chuck for compression
7 Receiving portion for compression
8 Chuck for elongation
9 Receiving portion for elongation
10 Fastening cords
X Length of five times the maximum outer diameter of the woven fabric
Y Irregularity of inner surface

DETAILED DESCRIPTION

The tubular woven fabric comprises warp yarns and weft yarns interwoven with each other, and does not require crimping, which is usually performed on a vascular prosthesis. Since no circumferential corrugations are provided, the variation in the outer diameter along the warp direction of the tubular woven fabric can be made to be within 10%.

The "variation in the outer diameter" as described in the expression "variation in the outer diameter is within 10%" is assessed as follows. First, the outer diameter is measured at five locations that are arranged at 50-mm intervals in the warp direction. Then, the minimum value is subtracted from the maximum value, and the difference is divided by the maximum value to determine the variation in the outer diameter, which is expressed in percentage.

The tubular woven fabric satisfies the relation represented by formula (1):

$$(L2-L1)/L1 \geq 0.1 \quad (1)$$

wherein

L1 is a gauge length of the tubular woven fabric when compressed in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric; and L2 is the gauge length of the tubular woven fabric when elongated in the warp direction by applying a stress of 0.01 cN/dtex.

For further improved stretch and flexibility, the value calculated by the above formula (L2−L1)/L1 is preferably 0.15 or more, more preferably 0.18 or more. The value is preferably up to 1.0.

When the relation between the gauge lengths L1 and L2 falls within the above range, the tubular woven fabric exhibits excellent stretch, flexibility and kink resistance (pliability). In more detail, when the tubular woven fabric is pliably bent, the inner side of the bent section of the tubular woven fabric is subjected to a stress in the compression direction and, simultaneously, the outer side of the bent section of the tubular woven fabric is subjected to a stress in the elongation direction. When the relation between the gauge lengths L1 and L2 falls within the above range, the outer side is sufficiently elongated with respect to the inner side, exhibiting excellent kink resistance. The stress of 0.01 cN/dtex applied to the tubular woven fabric to elongate or compress the tubular woven fabric typically corresponds to a stress applied by human hands to gently elongate or compress the tubular woven fabric in the warp direction. This indicates that, when the relation between the gauge lengths L1 and L2 falls within the above range, the tubular woven fabric exhibits good handling when bent by human hands, and also shows excellent stretch and flexibility.

The elongation of the tubular woven fabric should be such that, when a user gently stretches the tubular woven fabric by hand, the user can feel a response to elongation. Therefore, the elongation is preferably 30% or less when elongated in the warp direction by applying a stress of 0.01 cN/dtex. The elongation of the tubular woven fabric is more preferably 20% or less, further more preferably about 10%. The elongation of the tubular woven fabric when elongated in the warp direction by applying a stress of 0.01 cN/dtex is preferably 5% or more, more preferably 8% or more so that when a user gently stretches the tubular woven fabric by hand, the user can feel a response to elongation.

The change index (c) of the tubular woven fabric is calculated by formula (2):

$$\text{Change index, } c=(a-b)/a \quad (2)$$

wherein a is the maximum outer diameter of the tubular woven fabric when compressed in the warp direction by applying a stress of 0.01 cN/dtex, and b is the minimum outer diameter of the tubular woven fabric when elongated in the warp direction by applying a stress of 0.01 cN/dtex.

The change index (c) is preferably 0.03 or more and less than 0.2, more preferably 0.05 or more and less than 0.15.

When the relation between the maximum outer diameter (a) and the minimum outer diameter (b) falls within the above range, the change in the inner diameter of the tubular woven fabric will be small even when elongation and compression simultaneously occur due to bending or the like and, therefore, a constant flow passage is ensured.

The irregularity of the inner surface of the tubular woven fabric is preferably 100 μm or less, more preferably 80 μm or less, further more preferably 60 μm or less. The irregularity of the inner surface is preferably 3 μm or more to facilitate the formation of endothelium when the tubular woven fabric is used as a vascular prosthesis. The tubular woven fabric having an inner surface with an irregularity within the above range will not cause turbulent flow of a fluid passing through the tubular woven fabric even when the inner diameter is small. Especially when used as a vascular prosthesis having a small inner diameter, the tubular woven fabric provides advantages of causing no turbulent flow of blood or being less likely to cause thrombus formation.

The tubular woven fabric is preferably not crimped into circumferential corrugations. The tubular woven fabric having no circumferential corrugations has a smooth inner surface and does not cause turbulent flow even when a fluid passes through a narrow passage. Especially when used as a vascular prosthesis having a small inner diameter, the tubular woven fabric provides advantages of causing no turbulent flow of blood or being less likely to cause thrombus formation.

The phrase "having no circumferential corrugations" means that a tubular textile does not have circumferential corrugations formed by heat setting with an inserted core rod having spiral or annular corrugations, or that a tubular textile is not finished with pleating.

The warp and weft yarns used to produce the tubular woven fabric are preferably made of synthetic fibers such as nylon fibers and polyester fibers. The warp and weft yarns are more preferably the so-called non-elastic yarns. As used herein, the term "non-elastic yarn" refers to a yarn made of fibers not having the so-called rubber-like elasticity, and is a type of yarn different from the so-called elastic yarns having rubber-like elasticity, which are made of a material excellent in stretch and resilience such as a thermoplastic elastomer, including polyether elastomers, polysulfide elastomers, polyurethane elastomers and the like.

The non-elastic yarn herein is preferably a non-elastic polyester fiber yarn having strength and dimensional stability. Examples of the non-elastic polyester fiber yarn include a yarn made of fibers of polyethylene terephthalate, polybutylene terephthalate, polypropylene terephthalate, a copolymer thereof or the like.

Although such a non-elastic yarn is used, the tubular woven fabric has stretch.

The tubular woven fabric can be produced, for example, as follows.

In the weaving process, at least two types of warp yarns, i.e., warp yarn A and warp yarn B, are preferably used. These warp yarns are also preferably non-elastic yarns as described above.

The warp yarn A may be a yarn made of synthetic fibers such as nylon fibers and polyester fibers. Especially preferred is a non-elastic polyester fiber yarn having strength and dimensional stability. Examples of the non-elastic polyester fiber yarn include a yarn made of fibers of polyethylene terephthalate, polybutylene terephthalate, polypropylene terephthalate, a copolymer thereof or the like.

The warp yarn A, which constitutes the woven fabric, may be a directly spun microfiber yarn, or a microfiber yarn formed by removal of the sea component of sea-island composite fibers. The synthetic fiber yarn arranged in the warp direction is preferably a multifilament yarn containing filaments, wherein a part or all of the filaments have a diameter of 5 μm or less. When the diameter of the filaments is in the above range, the resulting tubular woven fabric has improved flexibility and a denser structure.

The warp yarn B is preferably a soluble yarn. The soluble yarn is a yarn made of fibers that are soluble in a solvent such as water and an alkaline solution. Specific examples of the soluble yarn include, but are not limited to, water-soluble fibers such as polyvinyl alcohol fibers; and easily alkali-soluble fibers such as polyester fibers containing a third copolymerized component such as isophthalic acid, sodium 5-sulfoisophthalate and methoxy polyoxyethylene glycol, and polylactic acid fibers. The warp yarn B may be a temporary yarn that is to be removed after weaving process.

The total fineness of each warp yarn is preferably 560 dtex or less, more preferably 235 dtex or less, further more preferably 100 dtex or less.

The weave density of the warp yarn A after post-processing is preferably 300 ends/inch (2.54 cm) or less, more preferably 280 ends/inch (2.54 cm) or less, further more preferably 250 ends/inch (2.54 cm) or less.

At least two types of weft yarns, i.e., weft yarn C and weft yarn D, are preferably used.

When at least two types of weft yarns are used, the tubular woven fabric is preferably a double layer woven fabric. Preferably, in the double layer woven fabric, the weft yarn C is arranged in the inner layer of the tubular woven fabric, and the weft yarn D is arranged in the outer layer of the tubular woven fabric.

The weft yarn C arranged in the inner layer and the weft yarn D arranged in the outer layer may each be a yarn made of synthetic fibers such as nylon fibers and polyester fibers, and is each preferably a non-elastic yarn. Especially preferred is a non-elastic polyester fiber yarn, which has strength and dimensional stability. Examples of the non-elastic polyester fiber yarn include a yarn made of fibers of polyethylene terephthalate, polybutylene terephthalate, polypropylene terephthalate, a copolymer thereof or the like.

The weft yarn C may be a directly spun microfiber yarn and may be arranged as it is in the inner layer in the weaving process. Alternatively, the weft yarn C may be a sea-island composite fiber yarn and may be arranged in the inner layer in the weaving process and, subsequently, the sea component may be removed to give microfibers. The synthetic fiber yarn arranged as the weft yarn C is preferably a multifilament yarn containing filaments, wherein a part or all of the filaments have a diameter of 5 μm or less. When the diameter of the filaments is in the above range, the resulting tubular woven fabric has improved flexibility and a denser structure.

The diameter of filaments contained in the weft yarn D arranged in the outer layer is preferably 10 to 20 μm. When the diameter of the filaments is in the above range, the outer layer is stiffer than the inner layer, is resistant to deterioration by hydrolysis, and has improved durability.

The total fineness of each weft yarn is preferably 560 dtex or less, more preferably 235 dtex or less, further more preferably 100 dtex or less.

The weave density of each weft yarn after post-processing is preferably 200 picks/inch (2.54 cm) or less, more preferably 180 picks/inch (2.54 cm) or less, further more preferably 150 picks/inch (2.54 cm) or less.

In the weaving process, preferably, the tension of the warp yarn B is high, whereas the tension of the warp yarn A is low to the extent that lowering of the tension does not prevent the shedding of the warp yarns. For example, the tension of the warp yarn B is preferably 0.5 to 1.5 cN/dtex, and the tension of the warp yarn A is preferably 0.05 to 0.15 cN/dtex. The warp yarn A and the warp yarn B are preferably arranged in an alternating pattern of 2 to 10 ends of the warp yarn A and one end of the warp yarn B.

Generally, in a weaving process for a high-density woven fabric, when the warp tension is lowered to increase the crimp percentage of the warp yarns, the weft density is difficult to increase due to possible occurrence of bumping (slack pick). However, according to the above example, the weft yarns are firmly held by the warp yarn A with the warp yarn B serving as a fulcrum and, in this way, bumping is prevented. Consequently, the crimp percentage of the warp yarn A can be increased, and by removal of the warp yarn B after weaving, flexibility is imparted to the tubular woven fabric.

The warp yarn B is preferably arranged between the weft yarn C arranged in the inner layer and the weft yarn D arranged in the outer layer.

The at least two types of weft yarns, i.e., the weft yarn C and the weft yarn D arranged in the inner layer and the outer layer of the tubular woven fabric, respectively, have different circumferences, which leads to structural strain. Due to the structural strain, the tubular woven fabric has an elongation capacity.

The inner diameter of the tubular woven fabric is preferably 100 mm or less, more preferably 50 mm or less, further more preferably 10 mm or less. The inner diameter of the tubular woven fabric is preferably at least about 1.5 mm for the weaving process to be successful.

The post-processing preferably includes, for example, the following steps. The example below exemplifies when the inner diameter of the tubular woven fabric is 3 mm.

(a) Hot Water Washing

The tubular woven fabric is washed with hot water to remove oil on the yarns and to allow the warp yarn B to shrink. Hot water washing is preferably performed at 80 to 98° C. for 15 to 40 minutes.

(b) Pre-Heat Setting

The dimensions of the warp yarn A having an increased crimp percentage due to shrinkage of the warp yarn B are stabilized by pre-heat setting. A round rod with an outer diameter of 2.8 mm is inserted into the tubular woven fabric, then both ends of the fabric are fastened on the rod with a wire or another material, and the tubular woven fabric is heated. The pre-heat setting is preferably performed at 160 to 190° C. for 3 to 10 minutes. The round rod may be made of, for example, SUS.

(c) Removal of Sea Component

As needed, the sea component of the warp yarn A and the weft yarn C is removed, and the warp yarn B is dissolved and removed.

The removal of the sea component and the dissolving and removal of the warp yarn B are performed by the following steps.

(c-1) Acid Treatment

The sea component of the sea-island composite fibers is made brittle by acid treatment. The acid may be, for example, maleic acid. The acid treatment is preferably performed at a concentration of 0.1 to 1% by mass at 100 to 150° C. for 10 to 50 minutes. When sea-island composite fibers are not used, acid treatment can be omitted.

(c-2) Alkali Treatment

The sea component of the sea-island composite fibers that has been made brittle by the acid treatment as well as the soluble yarn are dissolved by alkali treatment. The alkali may be, for example, sodium hydroxide. The alkali treatment is preferably performed at a concentration of 0.5 to 2% by mass at 70 to 98° C. for 60 to 100 minutes.

(d) Heat Setting (First Stage)

The first heat setting is performed to fully restore the crimp of the warp yarn that has been relaxed by the sea component removal. A round rod with an outer diameter of 3 mm is inserted into the tubular woven fabric. The tubular woven fabric is compressed as much as possible in the warp direction to the extent that wrinkles do not appear, and both ends of the fabric are fastened on the rod with a wire or another material. The fabric is then heated. The first heat setting is preferably performed at 160 to 190° C. for 3 to 10 minutes. The round rod may be made of, for example, SUS.

(e) Heat Setting (Second Stage)

The second heat setting is performed on the tubular woven fabric to provide a shrinkage allowance and stabilize the bending points of the crimp. The second heat setting may be omitted. A round rod with an outer diameter of 3 mm is inserted into the tubular woven fabric. The tubular woven fabric is elongated by 20 to 50% in the warp direction, and both ends of the fabric are fastened on the rod with a wire or another material. The fabric is then heated. The second heat setting is preferably performed at a temperature 10 to 20° C. lower than the first heat setting temperature for 3 to 10 minutes. The round rod may be made of, for example, SUS.

The thus produced tubular woven fabric has a less irregular inner surface and exhibits excellent stretch, flexibility and kink resistance (pliability). The tubular woven fabric is useful as a transport hose for a fluid or a powder, as a protective hose for linear bodies such as wires, cables and conduits, as a tubular filter, or as a base material of a vascular prosthesis. The tubular woven fabric is especially suitable for use in a vascular prosthesis.

When used as a vascular prosthesis, the tubular woven fabric preferably has a layer of an antithrombogenic material on the inner surface that is to be in contact with blood. The antithrombogenic material layer is preferably formed by binding a compound having anticoagulant activity to the inner surface. As used herein, the term "antithrombogenic" refers to a property that prevents blood coagulation on a surface in contact with blood, for example, the ability to inhibit platelet aggregation or blood coagulation that proceeds through activation of blood coagulation factors such as thrombin. The antithrombogenic material layer may be formed by any method, including but not limited to, a method involving covalent binding of heparin or a heparin derivative to a modified inner surface of the tubular woven fabric (JP 2009-545333 A, JP Patent No. 4152075 and JP Patent No. 3497612); a method involving ionic binding of heparin or a heparin derivative to the inner surface of the tubular woven fabric, and a method involving applying heparin or a heparin derivative contained in a gel such as collagen and gelatin, to the inner surface of the tubular woven fabric (JP Patent No. 3799626 and JP H08-24686 B); a method involving coating of the inner surface of the tubular woven fabric with a segmented polyurethane by impregnating the tubular woven fabric with the segmented polyurethane dissolved in an organic solvent (JP H07-265338 A); a method involving attachment of a compound that inhibits blood coagulation factors involved in blood coagulation reaction or a compound that inhibits thrombin or other factors involved in thrombus formation to the inner surface of the tubular woven fabric (JP Patent No. 4461217, WO 08/032758 and WO 12/176861); and other methods. Of these methods, preferred is a method involving ionic binding of heparin or a heparin derivative to the inner surface of the tubular woven fabric.

The antithrombogenic material is preferably a compound having anticoagulant activity. The compound having anticoagulant activity may be any compound that has inhibitory effect on platelet aggregation or blood coagulation that proceeds through the activation of blood coagulation factors such as thrombin. Examples of the compound include aspirin, clopidogrel sulfate, prasugrel sulfate, ticlopidine hydrochloride, dipyridamole, cilostazol, beraprost sodium, limaprost alfadex, sodium ozagrel, sarpogrelate hydrochloride, ethyl icosapentate, trapidil, warfarin potassium, heparin sodium, heparin potassium, dalteparin sodium, parnaparin sodium, reviparin sodium, rivaroxaban, apixaban, edoxaban, dabigatran, argatroban, dextran sulfate, polyvinyl sulfonate, polystyrene sulfonate and the like. Of these compounds, preferred is a sulfur-containing anionic compound having anticoagulant activity. The antithrombogenic material preferably further contains a cationic polymer. In particular, the antithrombogenic material more preferably contains a cationic polymer containing, as a monomer unit, a compound selected from the group consisting of alkyleneimines, vinyl amines, allylamine, lysine, protamines, and diallyl dimethyl ammonium chloride.

These monomer units have a cationic nitrogen atom, and their polymers are cationic. On the other hand, the sulfur-containing compound having anticoagulant activity is anionic, and can therefore bind to the cationic polymer by ionic bonding. Examples of the sulfur-containing anionic compound having anticoagulant activity include heparin and heparin derivatives, dextran sulfate, polyvinyl sulfonate, and polystyrene sulfonate. Preferred are heparin and heparin derivatives. The heparin and heparin derivatives may be purified or unpurified, and are not particularly limited as long as they inhibit blood coagulation reaction. Examples of the heparin and heparin derivatives include heparin that is commonly used for clinical applications, unfractionated heparin, low-molecular-weight heparin, and heparin with high affinity to antithrombin III. Specific examples of heparin include "heparin sodium" (Organon API, Inc.) and the like.

The cationic polymer may exhibit hemolytic toxicity and the like due to its cationic properties. Therefore, elution of the cationic polymer into the blood is not desirable. Accordingly, the cationic polymer is preferably bound to, more preferably covalently bound to, the warp and weft yarns that constitute the tubular woven fabric having an inner surface to be in contact with blood.

As used herein, the term "covalent bond" means a chemical bond formed by sharing of electrons between atoms. In particular, the covalent bond herein refers to a covalent bond between a carbon, nitrogen, oxygen or sulfur atom of the polymer that constitutes the antithrombogenic material and a carbon, nitrogen, oxygen or sulfur atom on the surface of the base material. The covalent bond may be a single bond or a multiple bond. Examples of the covalent bond include, but are not limited to, an amine bond, an azide bond, an amide bond, an imine bond and the like. Of these, an amide bond is preferred because the covalent bond is easy to form and the bond has high stability and other advantages.

The cationic polymer may be a homopolymer or a copolymer. When the cationic polymer is a copolymer, the copolymer may be a random copolymer, a block copolymer, a graft copolymer, or an alternating copolymer. Of these, a block copolymer containing successively repeating units containing a nitrogen atom is preferred because strong ionic bonds are formed by interaction between the blocks and the sulfur-containing anionic compound having anticoagulant activity.

The term "homopolymer" as used herein means a macromolecular compound obtained by polymerization of a single type of monomer unit. The term "copolymer" as used herein means a macromolecular compound obtained by copolymerization of two or more types of monomers. The term "block copolymer" as used herein means a copolymer having a molecular structure in which at least two types of polymers having different repeating units are covalently bound to each other to form a longer chain. The term "block" as used herein means each of the at least two types of polymers that have different repeating units and constitute the block copolymer.

The cationic polymer herein may be linear or branched. A branched cationic polymer is preferred because it can form a large number of more stable ionic bonds together with the sulfur-containing anionic compound having anticoagulant activity.

The cationic polymer herein has at least one functional group selected from primary, secondary and tertiary amino groups and a quaternary ammonium group. Of these, the cationic polymer having a quaternary ammonium group is preferred because a quaternary ammonium group forms stronger ionic interaction with the sulfur-containing anionic compound having anticoagulant activity than a primary, secondary or tertiary amine group, and therefore allows easier control of the elution rate of the sulfur-containing anionic compound having anticoagulant activity.

The number of carbon atoms in the three alkyl groups of the quaternary ammonium group is not particularly limited. However, the number of carbon atoms contained in the three alkyl groups should be selected to ensure that the quaternary ammonium group does not have high hydrophobicity or large steric hindrance so that the quaternary ammonium group effectively forms ionic bonds with the sulfur-containing anionic compound having anticoagulant activity. The number of carbon atoms contained in the three alkyl groups should also be selected to ensure that hemolytic toxicity is minimized. Accordingly, the number of carbon atoms contained in a single alkyl group bound to the nitrogen atom of the quaternary ammonium group is preferably 1 to 12, more preferably 2 to 6. The number of carbon atoms contained in each of the three alkyl groups bound to the nitrogen atom of the quaternary ammonium group may be the same as or different from each other.

The cationic polymer herein is preferably a polyalkyleneimine. Use of a polyalkyleneimine as the cationic polymer is advantageous in that it adsorbs a large amount of the sulfur-containing anionic compound having anticoagulant activity by ionic interaction. Examples of the polyalkyleneimine include polyethyleneimine (hereinafter called "PEI"), polypropyleneimine, polybutyleneimine, and alkoxylated polyalkyleneimine. Preferred is PEI.

Specific examples of PEI include "LUPASOL" (registered trademark) (BASF SE), and "EPOMIN" (registered trademark) (Nippon Shokubai Co., Ltd.). The PEI may be a copolymer with another monomer or a modified PEI polymer as long as the desired effects are not impaired. The term "modified polymer" as used herein means a polymer that has the same constituent monomers as in the original cationic polymer but some of the constituent monomers have undergone, for example, radical decomposition or recombination by irradiation as described later.

If the weight average molecular weight of the cationic polymer is excessively small, the molecular weight of the cationic polymer is smaller than that of the sulfur-containing anionic compound having anticoagulant activity. Consequently, stable ionic bonds cannot be formed and the desired antithrombogenicity is less likely to be achieved. On the other hand, if the weight average molecular weight of the cationic polymer is excessively large, the sulfur-containing anionic compound having anticoagulant activity is encapsulated in the cationic polymer, and the antithrombogenic material is buried under the cationic polymer. Accordingly, the weight average molecular weight of the cationic polymer is preferably 600 to 2,000,000, more preferably 1,000 to 1,500,000, further more preferably 10,000 to 1,000,000. The weight average molecular weight of the cationic polymer can be measured by, for example, gel permeation chromatography or the light scattering method.

The production process of the antithrombogenic material will be described below. The tubular woven fabric serving as a base material may be coated with the antithrombogenic material by, for example, immersing the base material in a solution containing the sulfur-containing anionic compound having anticoagulant activity and a polymer containing, as a monomer unit, a compound selected from the group consisting of alkylene imines, vinyl amines, allylamine, lysine, protamines, and diallyl dimethyl ammonium chloride. Alternatively, the sulfur-containing anionic compound having anticoagulant activity may be partially or fully reacted with the polymer to give an antithrombogenic material, and then the inner surface of the base material may be coated with the antithrombogenic material to form an antithrombogenic material layer on the inner surface of the base material.

To achieve efficient antithrombogenicity on the surface of the base material, preferred is a method including the first coating step of covalently binding the cationic polymer containing, as a monomer unit, a compound selected from the group consisting of alkyleneimines, vinyl amines, allylamine, lysine, protamines, and diallyl dimethyl ammonium chloride to the inner surface of the base material, and the second coating step of ionically binding the sulfur-containing anionic compound having anticoagulant activity to the cationic polymer.

When the cationic polymer contains primary, secondary and/or tertiary amino groups, the step of quaternizing the cationic polymer to form a quaternary ammonium polymer may be performed after the first coating step to form strong ionic interaction between the polymer and the sulfur-containing anionic compound having anticoagulant activity and to easily control the elution rate of heparin.

The production process of the antithrombogenic material by using the above method will be described in more detail below, which method includes the first coating step of covalently binding the cationic polymer containing, as a monomer unit, a compound selected from the group consisting of alkyleneimines, vinyl amines, allylamine, lysine, protamines, and diallyl dimethyl ammonium chloride to the inner surface of the base material, and the second coating step of ionically binding the sulfur-containing anionic compound having anticoagulant activity to the cationic polymer.

The covalent binding of the cationic polymer to the inner surface of the base material may be performed by any method. When the base material has a functional group (e.g., hydroxy, thiol, amino, carboxyl, aldehyde, isocyanate, and/or thioisocyanate group and the like), the cationic polymer may be chemically reacted with the functional group to form covalent bonds. For example, when the inner surface of the base material has a carboxyl group and the like, the polymer having a hydroxy group, a thiol group, an amino group and the like may be covalently bound to the inner surface of the base material; or alternatively, a compound having a hydroxy group, a thiol group, an amino group and the like is first covalently bound to the polymer, and then the polymer may be covalently bound to the inner surface of the base material having a carboxyl group and the like.

When the base material has no functional group, the inner surface of the base material may be treated by plasma, corona discharge and the like, and then the cationic polymer may be covalently bound to the base material; or alternatively, the inner surface of the base material and the cationic polymer may be irradiated to generate radicals, followed by the recombination reaction to form covalent bonds between the inner surface and the cationic polymer. The radiation may typically be γ-rays or an electron beam. When γ-rays are used, the activity of the γ-radiation source is preferably 2,500,000 to 10,000,000 Ci, more preferably 3,000,000 to 7,500,000 Ci. When an electron beam is used, the accelerating voltage of the electron beam is preferably 5 MeV or more, more preferably 10 MeV or more. The radiation dose is preferably 1 to 50 kGy, more preferably 5 to 35 kGy. The irradiation temperature is preferably 10 to 60° C., more preferably 20 to 50° C.

When the covalent bonds are formed by irradiation, an antioxidant may be used to control the amount of the radicals generated. As used herein, the term "antioxidant" refers to a molecule that readily donates an electron to another molecule. The antioxidant employed is not limited to a particular type, and examples thereof include water-soluble vitamins such as vitamin C; polyphenols; alcohols such as methanol, ethanol, propanol, ethylene glycol, propylene glycol and glycerol; sugars such as glucose, galactose, mannose and trehalose; inorganic salts such as sodium hydrosulfite, sodium pyrosulfite and sodium dithionite; uric acid; cysteine; glutathione; and buffering agents such as bis(2-hydroxyethyl)iminotris(hydroxymethyl)methane (hereinafter called "Bis-Tris"). Preferred are methanol, ethanol, propylene glycol and Bis-Tris, and more preferred are propylene glycol and Bis-Tris, all of which are easy to handle, do not remain as a residue and have other advantages. The antioxidants may be used alone or in combination of two or more types. The antioxidants are preferably added to an aqueous solution.

When polyester fibers are used in the tubular woven fabric as constituents, the cationic polymer may be contacted with the tubular woven fabric under heating to introduce covalent bonds between the polymer and the polyester fibers by aminolysis reaction. The introduction of covalent bonds can be done by a different method. Alternatively, ester bonds on the inner surface of the base material may be hydrolyzed by acid or alkali treatment to form carboxyl groups, and the carboxyl groups on the inner surface may be allowed to undergo condensation reaction with amino groups present on the cationic polymer to form covalent bonds. In the above methods, the cationic polymer may be directly contacted with the inner surface of the base material and allowed to react; or the cationic polymer may first be dissolved in a solvent, then contacted with the inner surface of the base material and allowed to react. The solvent is preferably water, an alcohol and the like, and especially preferred is water, which is easy to handle, does not remain as a residue and has other advantages. Yet alternatively, the constituent monomers of the cationic polymer may be contacted with the inner surface of the base material and then polymerized, and allowed to react with the inner surface to form covalent bonds.

The heating may be performed by any method, including but not limited to, electric heating, microwave heating, far-infrared heating and the like. When covalent bonds are introduced between the polyester fibers and the cationic polymer by aminolysis reaction, the heating temperature is preferably from a temperature near the glass transition point to the melting point.

We found it important that the step of hydrolyzing and oxidizing ester bonds on the inner surface of the base material is performed before the first coating step. Specifically, the hydrolyzing and oxidizing step is suitably performed by treating the inner surface with an acid or alkali and an oxidant. To increase the amount of the cationic polymer coating to enhance antithrombogenicity without inducing activation of complements, the hydrolyzing and oxidizing step is preferably performed by treating the inner surface with an acid or alkali and an oxidant.

We also found that, when the hydrolyzing and oxidizing step of ester bonds on the inner surface of the base material is performed using an acid or alkali and an oxidant, a combination of an acid and an oxidant is most suitable. Alternatively, the inner surface of the base material may be treated with an alkali, followed by treatment with an acid and an oxidant.

The acid employed is not limited to a particular type, and examples thereof include inorganic acids such as hydrochloric acid, hydrobromic acid, hydroiodic acid, hypochlorous acid, chlorous acid, perchloric acid, sulfuric acid, fluorosulfonic acid, nitric acid, phosphoric acid, hexafluoroantimonic acid, tetrafluoroboric acid, chromic acid and boric acid; sulfonic acids such as methanesulfonic acid, ethanesulfonic acid, benzenesulfonic acid, p-toluenesulfonic acid, trifluoromethanesulfonic acid and sodium polystyrene sulfonate; carboxylic acids such as acetic acid, citric acid, formic acid, gluconic acid, lactic acid, oxalic acid and tartaric acid; vinyl carboxylic acids such as ascorbic acid and Meldrum's acid; nucleic acids such as deoxyribonucleic acids and ribonucleic acids; and the like. Preferred are hydrochloric acid and sulfuric acid that are easy to handle.

The base employed is not limited to a particular type, and examples thereof include hydroxides of alkali metals such as lithium hydroxide, sodium hydroxide, potassium hydroxide, rubidium hydroxide and cesium hydroxide; hydroxides of tetraalkylammoniums such as tetramethylammonium hydroxide and tetraethylammonium hydroxide; hydroxides of alkaline earth metals such as calcium hydroxide, strontium hydroxide, barium hydroxide, europium hydroxide and thallium hydroxide; hydroxides of ammine complexes such as guanidine compounds, diamminesilver(I) hydroxide and tetraamminecopper(II) hydroxide; trimethylsulfonium hydroxide; diphenyliodonium hydroxide; and the like. Preferred are lithium hydroxide, sodium hydroxide and potassium hydroxide that are easy to handle.

The oxidant employed is not limited to a particular type, and examples thereof include potassium nitrate; hypochlorous acid; chlorous acid; perchloric acid; halogens such as fluorine, chlorine, bromine and iodine; permanganates such as potassium permanganate, sodium permanganate trihydrate, ammonium permanganate, silver permanganate, zinc permanganate hexahydrate, magnesium permanganate, calcium permanganate and barium permanganate; ceric ammonium nitrate; chromic acid; dichromic acid; peroxides such as hydrogen peroxide solution; Tollens' reagent; sulfur dioxide; and the like. Preferred are permanganates that have adequate oxidant strength and moderately prevent deterioration of the antithrombogenic material.

Covalent binding of the cationic polymer to the inner surface of the tubular woven fabric containing polyester fibers can also be achieved by, for example, condensation reaction using a dehydration condensation agent or the like.

The dehydration condensation agent is not limited to a particular type, and examples thereof include carbodiimide compounds such as N,N'-dicyclohexylcarbodiimide, N,N'-diisopropylcarbodiimide, 1-ether-3-(3-dimethylaminopropyl)carbodiimide, 1-ether-3-(3-dimethylaminopropyl)carbodiimide hydrochloride (hereinafter called "EDC"), 1,3-bis(2,2-dimethyl-1,3-dioxolan-4-ylmethyl)carbodiimide, N-{3-(dimethylamino)propyl}-N'-ethylcarbodiimide, N-{3-(dimethyl amino)propyl}-N'-ethylcarbodiimide methiodide, N-tert-butyl-N'-ethylcarbodiimide, N-cyclohexyl-N'-(2-morpholinoethyl)carbodiimide metho-p-toluenesulfonate, N,N'-di-tert-butylcarbodiimide, and N,N'-di-p-tricarbodiimide; and triazine compounds such as 4-(4,6-dimethoxy-1,3,5-triazin-2-yl)-4-methylmorpholinium chloride n-hydrate (hereinafter called "DMT-MM").

The dehydration condensation agent may be used together with a dehydration condensation promoting agent. The dehydration condensation promoting agent employed is not limited to a particular type, and examples thereof include pyridine, 4-dimethylaminopyridine (hereinafter called "DMAP"), triethylamine, isopropylamine, 1-hydroxybenzotriazole and N-hydroxysuccinimide.

The cationic polymer, the dehydration condensation agent, and the dehydration condensation promoting agent may be mixed together to form an aqueous solution to initiate the condensation reaction, or may be separately added in an appropriate order to initiate the condensation reaction.

When the cationic polymer contains primary, secondary and/or tertiary amino groups, the step of quaternizing the polymer to form a quaternary ammonium polymer may be performed to form strong ionic interaction between the polymer and heparin or a heparin derivative and to easily control the elution rate of heparin.

Quaternization of the cationic polymer to form a quaternary ammonium polymer may be performed before the cationic polymer is covalently bound to the inner surface of the base material; or alternatively, quaternization of the cationic polymer to form a quaternary ammonium polymer may be performed after the cationic polymer is covalently bound to the inner surface of the base material. However, to form strong ionic interaction between the cationic polymer and the sulfur-containing anionic compound having anticoagulant activity, the quaternary ammonium groups of the cationic polymer are preferably present on the innermost surface of the antithrombogenic material, and therefore quaternization of the cationic polymer to form a quaternary ammonium polymer is preferably performed after the cationic polymer is covalently bound to the inner surface of the base material. Specifically, after covalent bonding to the inner surface of the base material, the cationic polymer may be directly contacted with an alkyl halide compound such as chloro ether and bromo ether, or a quaternary ammonium salt containing a glycidyl group, or may be contacted with an aqueous solution or an organic solvent containing such an alkyl halide compound or the quaternary ammonium salt.

The second coating step, in which the sulfur-containing anionic compound having anticoagulant activity is ionically bound to the cationic polymer, is preferably performed by contacting the cationic polymer with an aqueous solution of the sulfur-containing anionic compound, but the ionic bonding may be formed by a different method.

As a measure of the antithrombogenicity, the anti-factor Xa activity of the antithrombogenic material was determined. As used herein, the term "anti-factor Xa activity" refers to an index of the degree of inhibition of the activity of factor Xa that promotes the conversion from prothrombin to thrombin. By measuring the anti-factor Xa activity, the amount of heparin or a heparin derivative on the surface of the antithrombogenic material can be determined in terms of the activity unit of heparin or a heparin derivative. For the measurement, "TEST TEAM (registered trademark) Heparin S" (made by Sekisui Medical Co., Ltd.) was used.

If the anti-factor Xa activity is too low, this indicates that the amount of heparin or a heparin derivative on the surface of the antithrombogenic material is too small, and the desired antithrombogenicity cannot be achieved. On the other hand, if the anti-factor Xa activity is too high, the amount of heparin or a heparin derivative on the surface is sufficient to exhibit the desired antithrombogenicity, but the thickness of the antithrombogenic material may be too large and consequently the fine structure of the surface of the base material may be impaired. In other words, the total amount of heparin or a heparin derivative coated on the surface of the antithrombogenic material as assessed by the anti-factor Xa activity is preferably 10 mIU/mg to 20000 mIU/mg, more preferably 50 mIU/mg to 10000 mIU/mg, per unit weight of the base material. The total amount of heparin coating herein is determined by cutting the base material into a size of about 0.5 cm×1 cm, immersing the specimen in 5 mL of human normal plasma, agitating the specimen at 37° C. for 24 hours, measuring the amount of heparin eluted in the human normal plasma and the amount of heparin remaining on the surface of the base material, and summing up the amounts.

The vascular prosthesis preferably has a layer of a bioabsorbable material on the outer surface of the tubular woven fabric serving as a base material. The bioabsorbable material covering the outer surface of the tubular woven fabric functions to prevent blood from leaking from the inside of the vascular prosthesis. Therefore, to prevent leakage of blood from the vascular prosthesis after implantation into the body, the bioabsorbable material is essentially required not to be soluble in water not only at a temperature equal to or lower than the body temperature but also at a temperature equal to or higher than the body temperature. As used herein, the term "bioabsorbable" means that a material will degrade over time by hydrolysis, enzymolysis, phagocytosis by immune cells, and/or other actions, and the products of degradation will be absorbed in the body. The bioabsorbable material that has finished the role in preventing leakage of blood may degrade and be absorbed in the body. The bioabsorbable material layer desirably has adequate dimensional stability, follows the shape of the tubular woven fabric, and has a structure that is advantageous for prevention of leakage of blood. The bioabsorbable material, therefore, preferably has adequate thickness, and does not necessarily have a non-porous structure, and may have a porous structure containing micropores such as interconnected pores.

The bioabsorbable material is not limited to a particular type. However, since the bioabsorbable material desirably follows the shape of the tubular woven fabric and is desirably easy to apply to the tubular woven fabric, the bioabsorbable material is preferably a macromolecular compound, and may be a synthetic polymer or a natural polymer. The synthetic polymer is preferably one that has been clinically applied, including a homopolymer or copolymer containing a monomer unit selected from the group consisting of lactic acid, glycolic acid, caproic acid, oxalic acid, malonic acid, succinic acid, glutaric acid, maleic acid, fumaric acid, ethylene glycol, propylene glycol, vinylpyrrolidone and vinyl alcohol. The natural polymer is preferably a polysaccharide or a protein, and is especially preferably collagen, atelocollagen or gelatin, which has been clinically applied. The endotoxin content of the gelatin is preferably small to avoid unwanted inflammatory reaction in the body. The gelatin is more preferably BEMATRIX (registered trademark) Gelatin (LS-H or LS-W)(made by Nitta Gelatin, Inc.), or RM-Gelatin (RM-50, RM-100 or RM-100B)(made by Jellice Co., Ltd.).

When the vascular prosthesis is implanted in the body, the bioabsorbable material layer is preferably made of a macromolecular compound that is insoluble at the body temperature. To exhibit this characteristic, the macromolecular compound is preferably at least insoluble in water at 37° C. The macromolecular compound that is insoluble in water serving as the bioabsorbable material is suitably obtained by reducing the ratio of hydrophilic to non-hydrophilic components in the macromolecular compound, or by chemically or physically introducing a crosslinked structure. When the bioabsorbable material is a protein, the protein may be one that has been made insoluble in water by introducing chemical crosslinking, as known. Chemical crosslinking may be introduced by any method, including chemical crosslinking using a substance containing a bivalent functional group, and radiation crosslinking using, for example, γ-rays. The substance containing a bivalent functional group used in chemical crosslinking may be, but is not limited to, a substance containing two or more reactive functional groups selected from the group consisting of an amino group, a carboxyl group, a hydroxy group, a thiol group, an isocyanate group, an isothiocyanate group, an aldehyde group, an epoxy group and a guanidino group. Of such compounds, preferred is glutaraldehyde or formaldehyde, which has been clinically applied.

The thickness of the bioabsorbable material layer was determined by cutting the vascular prosthesis perpendicularly to the longitudinal direction to expose the cross section, and observing the cross section at 300-fold magnification with a scanning electron microscope (Miniscope TM3000 made by Hitachi High-Technologies Corporation). Specifically, the thickness of the bioabsorbable material layer is determined as follows. P1 is defined as a point on the boundary that lies on a yarn arranged on the outermost circumference of the tubular woven fabric and is in contact with the bioabsorbable material, which is present on the outer side opposite to the inner side facing the center of the vascular prosthesis. A tangent to the cross section of the tubular woven fabric is drawn passing through P1. Then, P2 is defined as a point where a line perpendicular to the tangent crosses the outer circumference of the bioabsorbable material. The length of the perpendicular line from P1 to P2 is measured at five locations. The mean value is taken as the thickness (μm) of the bioabsorbable material layer. The thickness of the bioabsorbable material layer is preferably 10 μm or more to enhance durability to the blood pressure, and is preferably 300 μm or less to enhance the flexibility of the vascular prosthesis. The thickness of the bioabsorbable material layer is especially preferably 30 μm to 200 μm.

The kink radius of the vascular prosthesis is preferably 15 mm or less. The vascular prosthesis having a kink radius in this range exhibits excellent resistance to buckling (kink resistance) after implantation into the body. The kink resistance can be assessed by forming a loop of the vascular prosthesis, then gradually reducing the diameter of the loop, and measuring the loop radius at the onset of kinking. The minimum loop radius at the onset of kinking when the diameter of the loop is gradually reduced is defined as the kink radius. The kink radius is determined by measuring the minimum loop radius at the onset of the kinking in accordance with the guidance of ISO 7198.

Water permeability was used as a measure of leakage of blood from the vascular prosthesis after implantation. A lower water permeability of the vascular prosthesis is better. The water permeability is preferably 10 mL/cm$^2$·min or less. The water permeability is determined in accordance with ISO 7198. The amount of water (mL) that oozes from the outer surface of the vascular prosthesis is measured by applying a pressure of 120 mmHg to the inner surface of the vascular prosthesis at 25° C., and expressed as the amount of water (mL) divided by unit area (cm$^2$) and by unit time (30 sec.).

EXAMPLES

Examples will be described below in comparison with Comparative Examples.

The various characteristics evaluated in the Examples were measured as follows.

(1) Fineness and Number of Filaments

The fineness was determined in accordance with 8.3.1 Fineness based on corrected mass (Method A) as specified in JIS L 1013:2010.

The number of filaments was determined in accordance with JIS L 1013:2010 8.4.

(2) Diameter of Filaments

The lateral surface of a multifilament yarn used in Examples and Comparative Examples was photographed at 400-fold magnification with a microscope VHX-2000 (KEYENCE CORPORATION) to determine the diameter of the filaments, which was expressed in μm. In a modified cross-section yarn such as a flat yarn, the lateral surface with a minimum width was measured.

(3) Inner Diameter of Tubular Woven Fabric

The inner diameter of a tubular woven fabric was determined in accordance with the guidance of ISO 7198. Briefly, a circular cone with a taper ratio of 1:10 or a smaller taper ratio was placed upright. A tubular woven fabric with one end cut in the radial direction was held above the cone with the end facing down, and allowed to vertically fall on the cone so that the apex of the cone was slipped into the tubular woven fabric. The diameter of the cone at the height where the lower end of the specimen was situated was measured.

The inner diameter was measured at five locations at 50-mm intervals in the warp direction by cutting the tubular woven fabric. The maximum and minimum values were used for analysis.

(4) Outer Diameter of Tubular Woven Fabric

The outer diameter of a tubular woven fabric was measured with a caliper.

The outer diameter was measured at five locations at 50-mm intervals in the warp direction without applying stress to the tubular woven fabric. The maximum and minimum values were used for analysis.

The variation in the outer diameter was determined by subtracting the minimum value from the maximum value, and dividing the difference by the maximum value.

(5) Gauge Length (L1) of Tubular Woven Fabric Under Compression and Gauge Length (L2) of Tubular Woven Fabric Under Elongation The maximum value of the outer diameter of a tubular woven fabric (the maximum outer diameter of the tubular woven fabric when measured without applying stress to the tubular woven fabric) was first determined by the method described in (4) above.

Figure 1:
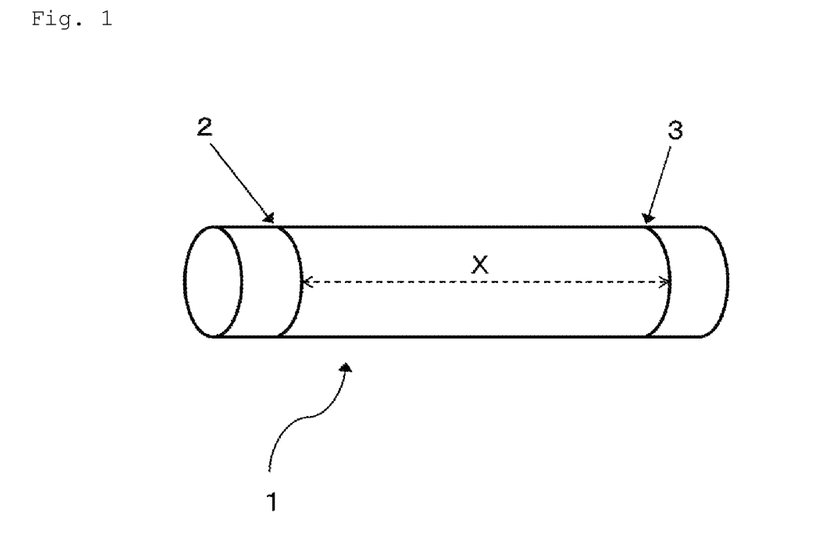
FIG. 1 is an explanatory diagram of drawing gauge marks on a tubular woven fabric.

FIG. 1 is an explanatory diagram for drawing gauge marks on a tubular woven fabric. As shown in FIG. 1, a first gauge mark (2) is drawn around the outer circumference of the tubular woven fabric (1) at 5 mm away from one end of the tubular woven fabric. A second gauge mark (3) is then drawn around the outer circumference of the woven fabric at a distance X, which is away from the first gauge mark (2) by a length of five times the maximum outer diameter of the tubular woven fabric. The tubular woven fabric (1) is cut in the radial direction at 5 mm outwardly away from the second gauge mark (3) (when the inner side of the gauge mark (3) is defined as the side where the arrows of the dotted line are located, the cutting position is located at the opposite side). The gauge length is defined as the length between the gauge marks (2, 3) as shown in FIG. 1.

Figure 2:
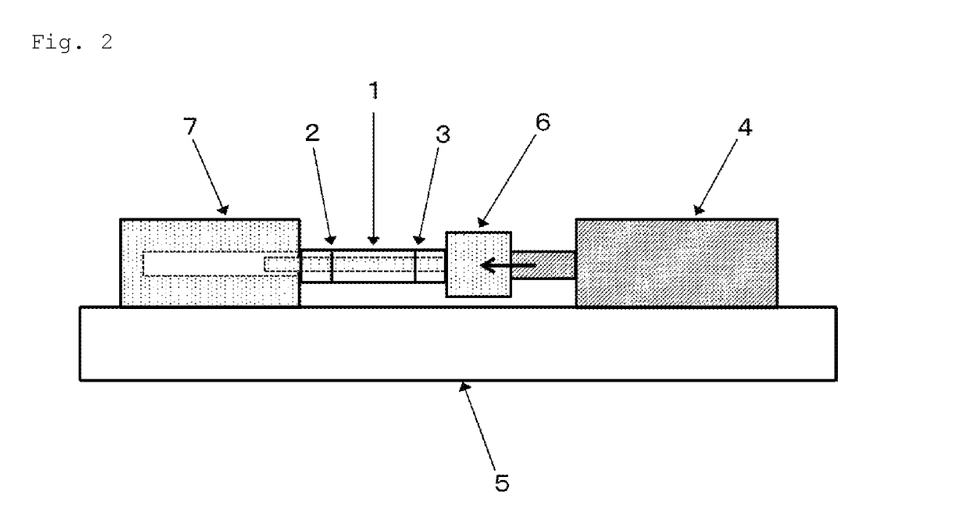
FIG. 2 is a schematic diagram of a device for measurement of a gauge length of a tubular woven fabric under compression.

FIG. 2 is a schematic diagram of a device for measurement of the gauge length of the tubular woven fabric under compression. In the device as shown in FIG. 2, HANDY DIGITAL FORCE GAUGE HF-1 (rated capacity: 10 N) made by Japan Instrumentation System Co., Ltd. is placed as a load gauge (force gauge) (4) on a platform (5). The load gauge (4) is equipped with a chuck for compression (6) having a core rod. A receiving portion for compression (7) having a hole capable of receiving the core rod is placed on the platform (5).

The tubular woven fabric (1) was placed on the above device by inserting the core rod of the chuck for compression (6) into the tubular woven fabric (1). The tubular woven fabric (1) was then compressed in the warp direction by applying a stress of 0.01 cN/dtex, and the gauge length (L1) (gauge length under compression) was measured with a caliper.

Figure 3:
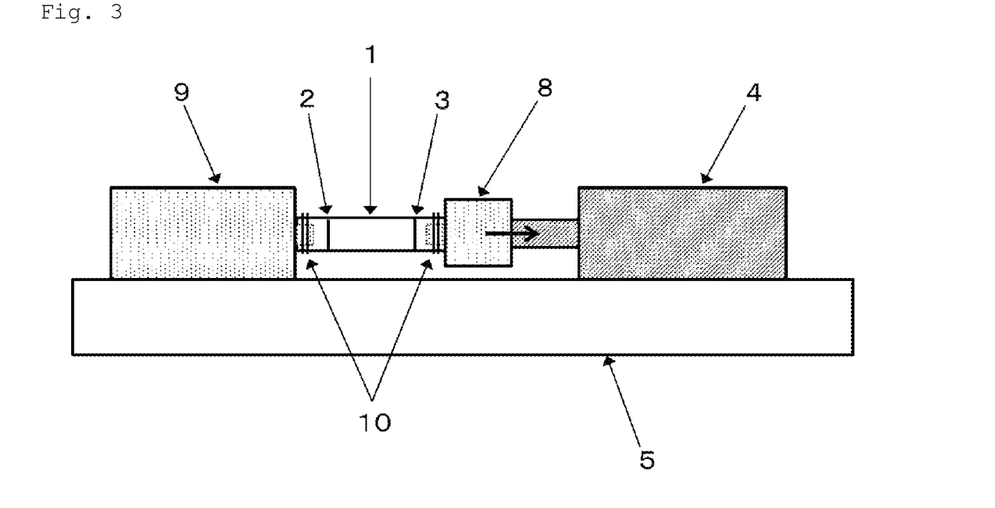
FIG. 3 is a schematic diagram of a device for measurement of a gauge length of a tubular woven fabric under elongation.

The outer diameter of the core rod of the chuck for compression (6) inserted into the tubular woven fabric (1) is a value that is calculated by subtracting "0.1 mm±0.03 mm" from the minimum inner diameter of the tubular woven fabric (1). The diameter of the hole of the receiving portion for compression (7) is equal to the minimum inner diameter of the tubular woven fabric. The "equal diameter" does not need to be exactly the same diameter, and may have a deviation of about ±0.03 mm. FIG. 3 is a schematic diagram of a device for measurement of the gauge length of the tubular woven fabric under elongation. In the device as shown in FIG. 3, HANDY DIGITAL FORCE GAUGE HF-1 (rated capacity: 10 N) made by Japan Instrumentation System Co., Ltd. is placed as a load gauge (force gauge) (4) on a platform (5). The load gauge (4) is equipped with a chuck for elongation (8) having a core rod capable of being inserted into the tubular woven fabric (1). A receiving portion for elongation (9) having a core rod capable of being inserted into the tubular woven fabric (1) is placed on the platform (5). The tubular woven fabric (1) was fastened on the core rods at each of the outer sides of the gauge marks (2, 3) with fastening cords (10). The tubular woven fabric (1) was then elongated in the warp direction by applying a stress of 0.01 cN/dtex, and the gauge length (L2) (gauge length under elongation) was measured with a caliper.

The measurement was repeated five times with different specimens, and the mean value was used for analysis.

The load expressed as a stress as described above was calculated by the following formula:

Load (cN)=0.01×fineness of warp yarns×number of warp ends.

(6) Outer Diameter of Tubular Woven Fabric Under Compression (a) and Outer Diameter of Tubular Woven Fabric Under Elongation (b)

In the same manner as in (5) above, a tubular woven fabric was compressed in the warp direction by applying a stress of 0.01 cN/dtex, and the outer diameter of the tubular woven fabric was measured with a caliper.

The measurement was repeated five times with different specimens, and the maximum value was taken as "the maximum outer diameter (a) (the outer diameter of the tubular woven fabric under compression (a))".

The tubular woven fabric was elongated in the warp direction by applying a stress of 0.01 cN/dtex, and the outer diameter of the tubular woven fabric was measured with a caliper.

The measurement was repeated five times with different specimens, and the minimum value was taken as "the minimum outer diameter (b) (the outer diameter of the tubular woven fabric under elongation (b))".

In each test, the outer diameter was measured at three locations: the center between the two gauge marks (2, 3) drawn on the tubular woven fabric (1), and 5 mm inside of each of the gauge marks. Since the measurement at each location was repeated five times with different specimens, the measurement was performed 15 times in total.

(7) Irregularity of Inner Surface of Tubular Woven Fabric

Figure 4:
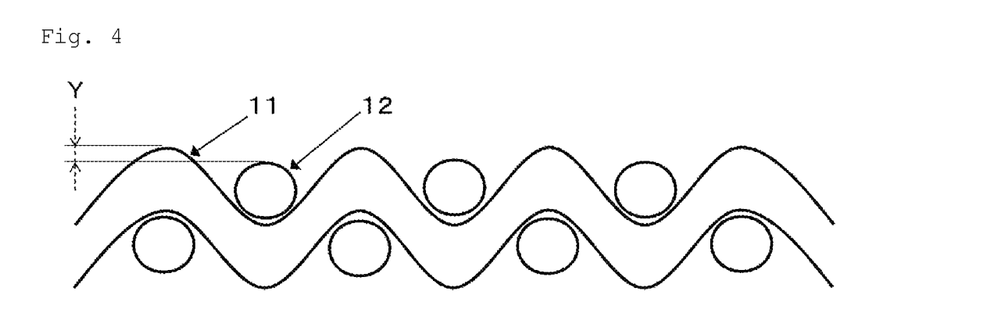
FIG. 4 is an explanatory diagram of the definition of the irregularity of the inner surface of a tubular woven fabric.

A tubular woven fabric was cut in half in the warp direction. The weftwise cross section was photographed at 150-fold magnification with an electron microscope, and the difference in height between the top of the warp yarn and the top of the adjacent weft yarn on the inner surface of the tubular woven fabric was determined. The definition of the irregularity of the inner surface of a tubular woven fabric will be explained with reference to FIG. 4. As used herein, the term "irregularity of the inner surface" refers to the difference (Y) in height between the adjacent warp (11) and weft (12) yarns exposed on the inner surface of the tubular woven fabric.

The measurement was repeated five times with different specimens, and the mean value was used for analysis. The mean value of the difference in height between the top surfaces of the warp and weft yarns as explained with reference to FIG. 4 was taken as "the irregularity of the inner surface of a tubular woven fabric".

(8) Weave Density

The weave density was determined in accordance with JIS L 1096:2010 8.6.1. A specimen was placed on a flat table, and unnatural wrinkles and tension were removed. The number of the warp and weft yarns in a length of 0.5 cm was counted at five different locations, and the mean value was calculated and expressed as the number of the yarns per 2.54 cm.

(9) Kink Resistance

The kink resistance was determined by measuring the kink radius in accordance with the guidance of ISO 7198. Briefly, a tubular woven fabric was formed into a loop, and the diameter of the loop was gradually decreased until apparent kinking occurred. A cylindrical mandrel with a known radius was placed in the loop to measure the radius. Internal pressure was not applied for the purpose of the evaluation of the genuine kink resistance of the tubular woven fabric.

Example 1

In weaving process, the following warp yarns (warp yarn A and warp yarn B) and weft yarns (weft yarn C and weft yarn D) were used.

Warp yarn A (sea-island composite fibers): polyethylene terephthalate fiber yarn, 66 dtex, 9 filaments (after removal of the sea component: 52.8 dtex, 630 filaments)

Warp yarn B (soluble yarn): easily alkali-soluble polyester fiber yarn copolymerized with sodium 5-sulfoisophthalate, 84 dtex, 24 filaments Weft yarn C (inner layer) (sea-island composite fibers): polyethylene terephthalate fiber yarn, 66 dtex, 9 filaments (after removal of the sea component: 52.8 dtex, 630 filaments)

Weft yarn D (outer layer): polyethylene terephthalate fiber yarn, 56 dtex, 18 filaments A tubular woven fabric with an inner diameter of 3 mm was woven using the above warp and weft yarns. The tension of the warp yarn B during weaving was 0.9 cN/dtex, and the tension of the warp yarn A during weaving was 0.1 cN/dtex. The weave density after post-processing was as follows: the warp yarn A, 201 ends/inch (2.54 cm); the weft yarn C, 121 picks/inch (2.54 cm); and the weft yarn D, 121 picks/inch (2.54 cm). The warp yarn A and warp yarn B were arranged in an alternating pattern of three ends of the warp yarn A and one end of the warp yarn B. The warp yarn B was arranged between the weft yarn C arranged in the inner layer and the weft yarn D arranged in the outer layer.

Post-processing was then performed in the following steps.

(a) Hot Water Washing

Hot water washing was performed at 98° C. for 20 minutes.

(b) Pre-Heat Setting

A round rod with an outer diameter of 2.8 mm was inserted into the tubular woven fabric. Both ends of the fabric were fastened on the rod with a wire, and the fabric was heated. The pre-heat setting was performed at 180° C. for 5 minutes. The round rod was made of SUS.

(c) Removal of Sea Component

The sea component of the warp yarn A and the weft yarn C was removed, and the warp yarn B was dissolved and removed.

(c-1) Acid Treatment

Maleic acid was used for acid treatment. The acid treatment was performed at a concentration of 0.2% by mass at 130° C. for 30 minutes.

(c-2) Alkali Treatment

Sodium hydroxide was used for alkali treatment. The alkali treatment was performed at a concentration of 1% by mass at 80° C. for 90 minutes.

(d) Heat Setting (First Stage)

A round rod with an outer diameter of 3 mm was inserted into the tubular woven fabric. The tubular woven fabric was compressed as much as possible in the warp direction to the extent that wrinkles did not appear. Both ends of the fabric were then fastened on the rod with a wire or another material. The fabric was then heated. The heat setting was performed at 180° C. for 5 minutes. The round rod was made of SUS.

(e) Heat Setting (Second Stage)

A round rod with an outer diameter of 3 mm was inserted into the tubular woven fabric. The tubular woven fabric was elongated by 30% in the warp direction, and both ends of the fabric were fastened on the rod with a wire or another material. The fabric was then heated. The heat setting was performed at 170° C. for 5 minutes. The round rod was made of SUS.

The characteristics of the thus produced tubular woven fabric are shown in Table 1.

The tubular woven fabric, when bent by hand, showed excellent handling, stretch and flexibility.

The tubular woven fabric had small variations in the outer diameter and in the inner diameter along the warp direction. Therefore, when sutured to another identical tubular woven fabric, the tubular woven fabric for use as a vascular prosthesis required no consideration on where to cut and was easily anastomosed to another identical tubular woven fabric.

Example 2

A tubular woven fabric was produced in the same manner as in Example 1 except that the inner diameter of the tubular woven fabric was 5 mm and the second heat setting was not performed.

The tubular woven fabric, when bent by hand, showed excellent handling, stretch and flexibility.

The tubular woven fabric had small variations in the outer diameter and in the inner diameter along the warp direction. Therefore, when sutured to another identical tubular woven fabric, the tubular woven fabric for use as a vascular prosthesis required no consideration on where to cut and was easily anastomosed to another identical tubular woven fabric.

The characteristics of the thus produced tubular woven fabric are shown in Table 1.

Example 3

A tubular woven fabric was produced in the same manner as in Example 1 except that the inner diameter of the tubular woven fabric was 7 mm and the elongation in the second heat setting was 20%.

The characteristics of the thus produced tubular woven fabric are shown in Table 1.

The tubular woven fabric, when bent by hand, showed excellent handling, stretch and flexibility.

The tubular woven fabric had small variations in the outer diameter and in the inner diameter along the warp direction. Therefore, when sutured to another identical tubular woven fabric, the tubular woven fabric for use as a vascular prosthesis required no consideration on where to cut and was easily anastomosed to another identical tubular woven fabric.

Comparative Example 1

A tubular woven fabric (inner diameter: 3 mm) with plain weave was woven using the warp yarn A and the weft yarn C used in Example 1. The tension of the warp yarn A was 0.9 cN/dtex. The weave density after post-processing was as follows: the warp yarn A, 201 ends/inch (2.54 cm); and the weft yarn C, 121 picks/inch (2.54 cm). The tubular woven fabric was then subjected to post-processing in the same manner as in Example 1.

The characteristics of the thus produced tubular woven fabric are shown in Table 1.

The tubular woven fabric was relatively difficult to bend by hand as compared to that produced in Example 1, and had poor stretch and flexibility.

The tubular woven fabric had small variations in the outer diameter and in the inner diameter along the warp direction. Therefore, when sutured to another identical tubular woven fabric, the tubular woven fabric for use as a vascular prosthesis required no consideration on where to cut and was easily anastomosed to another identical tubular woven fabric.

Comparative Example 2

A tubular woven fabric (inner diameter: 3 mm) was produced in the same manner as in Example 1 except that the tension of the warp yarn B during weaving was 0.9 cN/dtex and the tension of the warp yarn A during weaving was 0.9 cN/dtex.

The characteristics of the thus produced tubular woven fabric are shown in Table 1.

The tubular woven fabric was relatively difficult to bend by hand as compared to that produced in Example 1, and had poor stretch and flexibility.

The tubular woven fabric had small variations in the outer diameter and in the inner diameter along the warp direction. Therefore, when sutured to another identical tubular woven fabric, the tubular woven fabric for use as a vascular prosthesis required no consideration on where to cut and was easily anastomosed to another identical tubular woven fabric.

Comparative Example 3

In weaving process, warp yarn E and weft yarn F as described below were used.

Warp yarn E: polyethylene terephthalate fiber yarn, 66 dtex, 72 filaments

Weft yarn F: polyethylene terephthalate fiber yarn, 140 dtex, 144 filaments

A tubular woven fabric with an inner diameter of 7 mm was woven using the above warp and weft yarns. The tension of the warp yarn E during weaving was 0.9 cN/dtex. The weave density after post-processing was as follows: the warp yarn E, 180 ends/inch (2.54 cm); and the weft yarn F, 120 picks/inch (2.54 cm).

Post-processing was then performed in the following steps.

(a) Hot Water Washing

Hot water washing was performed at 98° C. for 20 minutes.

(b) Heat Setting

An ISO metric screw thread with an outer diameter of 7.0 mm was inserted in the tubular woven fabric. A polyethylene yarn was wound around the fabric at a tension of 1 kg so that the yarn ran along the grooves of the inserted thread. The fabric was then heated. The heat setting was performed at 170° C. for 30 minutes. The ISO metric screw thread was made of SUS.

The characteristics of the thus produced tubular woven fabric are shown in Table 1.

The tubular woven fabric, when bent by hand, showed excellent handling, stretch and flexibility.

The tubular woven fabric had large variations in the outer diameter and in the inner diameter along the warp direction. Therefore, when sutured to another identical tubular woven fabric, the tubular woven fabric for use as a vascular prosthesis required consideration on where to cut. The tubular woven fabric, when cut on a bias, was difficult to be anastomosed to another identical tubular woven fabric due to the irregularity.

Example 4

The tubular woven fabric of Example 1 was immersed in an aqueous solution of 5.0 wt % potassium permanganate (Wako Pure Chemical Industries, Ltd.) and 0.6 mol/L sulfuric acid (Wako Pure Chemical Industries, Ltd.) at 60° C. for 3 hours to allow hydrolysis and oxidation reaction to occur.

The tubular woven fabric was then immersed in an aqueous solution of 0.5 wt % DMT-MM Pure Chemical Industries, Ltd.) and 5.0 wt % PEI (LUPASOL (registered trademark) P; BASF SE) at 30° C. for 2 hours to covalently bind PEI to the inner surface of the tubular woven fabric of Example 1 via condensation reaction.

The tubular woven fabric was then immersed in a 1 wt % aqueous solution of ethyl bromide (Wako Pure Chemical Industries, Ltd.) in methanol at 35° C. for 1 hour. The solution was then heated to 50° C., and the reaction was continued for 4 hours to quaternize the PEI covalently bound to the tubular woven fabric of Example 1 to form a quaternary ammonium PEI.

Finally, the tubular woven fabric was immersed in an aqueous solution of 0.75 wt % heparin sodium (Organon API) and 0.1 mol/L sodium chloride (pH=4) at 70° C. for 6 hours to ionically bind heparin to the quaternary ammonium PEI. In this manner, a tubular woven fabric having an antithrombogenic material layer on the inner surface was produced. The total amount of heparin coated on the tubular woven fabric was 1100 mIU/mg.

Example 5

A lactic acid/glycolic acid copolymer was prepared at a concentration of 20 wt % (in chloroform as a solvent) as a bioabsorbable material. The copolymer was applied to the outer surface of the tubular woven fabric produced in Example 4, and dried at room temperature overnight to form a layer of the bioabsorbable material. The thickness of the bioabsorbable material layer was 65 μm. The water permeability of the tubular woven fabric having the bioabsorbable material layer was measured by applying a pressure of 120 mmHg to the inner surface at 25° C. and determined to be 0 mL/cm$^2$·min. The kink radius determined in accordance with the guidance of ISO 7198 was 15 mm.

Example 6

A lactic acid/ε-caprolactone copolymer was prepared at a concentration of 20 wt % (in tetrahydrofuran as a solvent) as a bioabsorbable material. The copolymer was applied to the outer surface of the tubular woven fabric produced in Example 4, and dried at 40° C. for 2 hours to form a layer of the bioabsorbable material. The thickness of the bioabsorbable material layer was 45 μm. The water permeability of the tubular woven fabric having the bioabsorbable material layer was measured by applying a pressure of 120 mmHg to the inner surface at 25° C. and determined to be 0 mL/cm$^2$·min. The kink radius determined in accordance with the guidance of ISO 7198 was 10 mm.

Example 7

A gelatin solution (BEMATRIX (registered trademark) Gelatin LS-H; made by Nitta Gelatin, Inc.) was prepared at a concentration of 30 wt % as a bioabsorbable material. The gelatin solution was applied to the outer surface of the tubular woven fabric produced in Example 4, and cooled at 4° C. for 1 hour to solidify the gelatin. The tubular woven fabric was immersed in a 0.2% glutaraldehyde solution for 30 minutes to crosslink the gelatin, and dried at 40° C. overnight. The thickness of the bioabsorbable material layer was 120 μm. The water permeability of the tubular woven fabric having the bioabsorbable material layer was measured by applying a pressure of 120 mmHg to the inner surface at 25° C. and determined to be 0 mL/cm$^2$·min. The kink radius determined in accordance with the guidance of ISO 7198 was 7 mm.

Example 8

The water permeability of the tubular woven fabric produced in Example 1 was measured by applying a pressure of 120 mmHg to the inner surface at 25° C. and determined to be 188 mL/cm$^2$·min.

TABLE 1

|  |  | Example 1 | Example 2 | Example 3 | Comparative Example 1 | Comparative Example 2 | Comparative Example 3 |
|---|---|---|---|---|---|---|---|
| Warp yarn A: fineness | dtex | 52.8 | 52.8 | 52.8 | 52.8 | 52.8 | — |
| Warp yarn A: number of filaments | ends | 630 | 630 | 630 | 630 | 630 | — |
| Warp yarn A: diameter of filaments | μm | 2.78 | 2.78 | 2.78 | 2.78 | 2.78 | — |
| Weft yarn C: fineness | dtex | 52.8 | 52.8 | 52.8 | 52.8 | 52.8 | — |
| Weft yarn C: number of filaments | picks | 630 | 630 | 630 | 630 | 630 | — |
| Weft yarn C: diameter of filaments | μm | 2.78 | 2.78 | 2.78 | 2.78 | 2.78 | — |
| Weft yarn D: fineness | dtex | 56 | 56 | 56 | — | 56 | — |
| Weft yarn D: number of filaments | picks | 18 | 18 | 18 | — | 18 | — |
| Weft yarn D: diameter of filaments | μm | 16.94 | 16.94 | 16.94 | — | 16.94 | — |
| Warp yarn E: fineness | dtex | — | — | — | — | — | 66 |
| Warp yarn E: number of filaments | ends | — | — | — | — | — | 72 |
| Warp yarn E: diameter of filaments | μm | — | — | — | — | — | 9.16 |
| Weft yarn F: fineness | dtex | — | — | — | — | — | 140 |
| Weft yarn F: number of filaments | picks | — | — | — | — | — | 144 |
| Weft yarn F: diameter of filaments | μm | — | — | — | — | — | 9.47 |
| Maximum inner diameter of woven fabric | mm | 3.05 | 5.07 | 7.02 | 3.01 | 3.05 | 9.82 |
| Minimum inner diameter of woven fabric | mm | 3.02 | 5.01 | 6.95 | 2.99 | 3.01 | 7.18 |
| Maximum outer diameter of woven fabric | mm | 3.76 | 5.81 | 7.75 | 3.22 | 3.46 | 10.11 |
| Minimum outer diameter of woven fabric | mm | 3.74 | 5.77 | 7.69 | 3.19 | 3.41 | 7.46 |
| Variation in outer diameter | % | 0.53 | 0.69 | 0.77 | 0.93 | 1.45 | 26.21 |
| Gauge length | mm | 18.8 | 29.05 | 38.75 | 16.1 | 17.3 | 50.55 |
| Gauge length under compression (L1) | mm | 16.5 | 28.2 | 34.8 | 16.1 | 17.3 | 19.6 |
| Gauge length under elongation (L2) | mm | 20.5 | 33.7 | 44.3 | 16.2 | 17.5 | 69.42 |
| (L2 − L1)/L1 | — | 0.24 | 0.20 | 0.27 | 0.01 | 0.01 | 2.54 |
| Outer diameter of woven fabric under compression (a) | mm | 3.96 | 6.05 | 8.17 | 3.23 | 3.46 | 10.33 |
| Outer diameter of woven fabric under elongation (b) | mm | 3.69 | 5.69 | 7.31 | 3.21 | 3.44 | 7.41 |
| Change index (c) | — | 0.07 | 0.06 | 0.11 | 0.01 | 0.01 | 0.28 |
| Irregularity of inner surface of tubular woven fabric | μm | 52 | 48 | 46 | 5 | 20 | 2640 |
| Kink radius | mm | 3 | 5 | 6 | 20 | 24 | 2 |

In Table 1, all of the warp yarn A, the weft yarn C, the weft yarn D, the warp yarn E and the weft yarn F are made of polyethylene terephthalate.

INDUSTRIAL APPLICABILITY

The tubular woven fabric can be suitably used as a vascular prosthesis, but the applications thereof are not limited thereto.

The invention claimed is:

1. A tubular woven fabric comprising a warp yarn A and weft yarns consisting of a weft yarn C and a weft yarn D, wherein warp yarns consisting of the warp yarn A and a warp yarn B and weft yarns consisting of the weft yarn C and the weft yarn D are interwoven with each other to obtain the tubular woven fabric by removal of the warp yarn B after weaving, wherein the warp yarn A, the weft yarn C and weft yarn D are non-elastic polyester yarns, and the warp yarn B is a soluble yarn made of fibers soluble in at least one of water or an alkaline solution, and the weft yarn C is arranged in the inner layer of the tubular woven fabric, and the weft yarn D is arranged in the outer layer of the tubular woven fabric, and the filaments constituting the weft yarn D have a larger diameter than the filaments constituting the weft yarn C, and satisfying Formula (1):

$$(L2-L1)/L1 \geq 0.1 \quad (1)$$

wherein

L1 is a gauge length of the tubular woven fabric when compressed in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric; and L2 is a gauge length of the tubular woven fabric when elongated in the warp direction by applying a stress of 0.01 cN/dtex, as determined after the outer diameter of the tubular woven fabric is measured without applying stress to the tubular woven fabric to determine a maximum outer diameter and then gauge marks are drawn around an outer circumference of the tubular woven fabric so that the gauge marks are separated by a length of five times the maximum outer diameter of the tubular woven fabric, wherein the warp yarns A are multifilament yarns containing filaments, and a part or all of the filaments have a diameter of 5 μm or less.

2. The tubular woven fabric according to claim 1, which has an inner surface with an unevenness of 100 μm or less.

3. The tubular woven fabric according to claim 1, which has no circumferential corrugations.

4. The tubular woven fabric according to claim 1, wherein the weft yarns C are multifilament yarns containing filaments, wherein a part or all of the filaments have a diameter of 5 μm or less, wherein the diameter of filaments contained in the weft yarn D is in the range of 10 to 20 μm.

5. A vascular prosthesis comprising the tubular woven fabric according to claim 1 as a base material, the base material having an inner surface having a layer of an antithrombogenic material.

6. The vascular prosthesis according to claim 5, wherein the antithrombogenic material contains a sulfur-containing anionic compound having anticoagulant activity.

7. The vascular prosthesis according to claim 5, wherein the antithrombogenic material contains a cationic polymer containing, as a monomer unit, a compound selected from the group consisting of alkylene imines, vinyl amines, allylamine, lysine, protamines, and diallyl dimethyl ammonium chloride, and wherein the cationic polymer is covalently bound to warp and weft yarns constituting the tubular woven fabric having an inner surface to be in contact with blood.

8. A vascular prosthesis comprising the tubular woven fabric according to claim 1 as a base material, the base material having an outer surface having a further layer of a bioabsorbable material that will degrade by hydrolysis, enzymolysis, phagocytosis by immune cells or other action and resulting products of the degrading are absorbable.

9. The vascular prosthesis according to claim 8, which has a kink radius of 15 mm or less.

10. The vascular prosthesis according to claim 9, which has a water permeability of 10 $mL/cm^2$ min or less as measured by applying a pressure of 120 mmHg to an inner surface of the vascular prosthesis at 25° C.

11. The vascular prosthesis according to claim 8, wherein the bioabsorbable material is a homopolymer or copolymer containing a monomer unit selected from the group consisting of lactic acid, glycolic acid, caproic acid, oxalic acid, malonic acid, succinic acid, glutaric acid, maleic acid, fumaric acid, ethylene glycol, propylene glycol, vinylpyrrolidone and vinyl alcohol.

12. The vascular prosthesis according to claim 8, wherein the bioabsorbable material is a polysaccharide or a protein.

13. The vascular prosthesis according to claim 12, wherein the protein is selected from the group consisting of collagen, atelocollagen and gelatin.

* * * * *